US012678192B2

(12) United States Patent
Fintelmann

(10) Patent No.: US 12,678,192 B2
(45) Date of Patent: Jul. 14, 2026

(54) PERCUTANEOUS LUNG ABLATION CLOSURE DEVICE

(71) Applicant: The General Hospital Corporation, Boston, MA (US)

(72) Inventor: Florian J. Fintelmann, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 352 days.

(21) Appl. No.: 18/305,687

(22) Filed: Apr. 24, 2023

(65) Prior Publication Data

US 2023/0338059 A1 Oct. 26, 2023

Related U.S. Application Data

(60) Provisional application No. 63/333,635, filed on Apr. 22, 2022.

(51) Int. Cl.
*A61B 17/34* (2006.01)
*A61B 10/02* (2006.01)
*A61B 17/00* (2006.01)

(52) U.S. Cl.
CPC ...... *A61B 17/3423* (2013.01); *A61B 10/0233* (2013.01); *A61B 2017/00646* (2013.01)

(58) Field of Classification Search
CPC ...... A61B 18/1477; A61B 2018/00577; A61B 2018/1475; A61B 17/3421; A61B 2018/00023; A61B 2018/00541; A61B 2018/00642; A61B 2018/00791; A61B 2018/1465; A61B 10/0233; A61B 17/0057; A61B 17/3423; A61B 18/04; A61B 18/14; A61B 18/1492; A61B 18/16; A61B 2017/00646; A61B 2017/00809; A61B 2017/00867; A61B 2018/00029;
(Continued)

(56) References Cited

U.S. PATENT DOCUMENTS 8,734,435 B2 5/2014 Greenberg et al.
10,335,234 B2 7/2019 Greenberg et al.
(Continued)

FOREIGN PATENT DOCUMENTS

AU 2003299954 B2 * 8/2009 .......... A61K 38/212
WO 2021188112 A1 9/2021

*Primary Examiner* — Jon Eric C Morales
(74) *Attorney, Agent, or Firm* — QUARLES & BRADY LLP

(57) ABSTRACT

In accordance with some non-limiting examples of the disclosed subject matter, a method of reducing pneumothorax in a percutaneous lung procedure using a cannula having a lumen extending from a first opening to a second opening and having a third opening arranged along a length of the lumen is provided. The reservoir containing a liquid sealant is coupled to the third opening of the cannula. While the cannula is arranged within a subject such that the second opening of the lumen opens into a pleural cavity of the subject, the liquid sealant is injected from the reservoir into the lumen such that the liquid sealant flows out of the second opening of the cannula into the pleural cavity. With liquid sealant sealing the pleural cavity, the cannula is withdrawn from the pleural cavity such that air is unable to infiltrate the pleural cavity by way of the liquid sealant.

19 Claims, 10 Drawing Sheets

(58) Field of Classification Search
    CPC .......... A61B 2018/00071; A61B 2018/00077;
                    A61B 2018/00083; A61B 2018/00702;
                    A61B 2018/00875; A61B 2018/00982;
                A61B 2018/1253; A61B 2018/126; A61B
                    2018/1427; A61B 2018/143; A61B
                    2018/1495; A61B 2018/162; A61B
                    2018/167; A61B 2218/001; A61B
                                            2218/002
    See application file for complete search history.

(56)                    References Cited

U.S. PATENT DOCUMENTS

| | | | |
|---|---|---|---|
| 11,344,357 B2 | 5/2022 | Garabedian et al. | |
| 2003/0032936 A1 | 2/2003 | Lederman | |
| 2021/0236191 A1 | 8/2021 | Wang et al. | |
| 2022/0133397 A1* | 5/2022 | Morris ............... | A61B 18/1477 |
| | | | 606/41 |

* cited by examiner

500

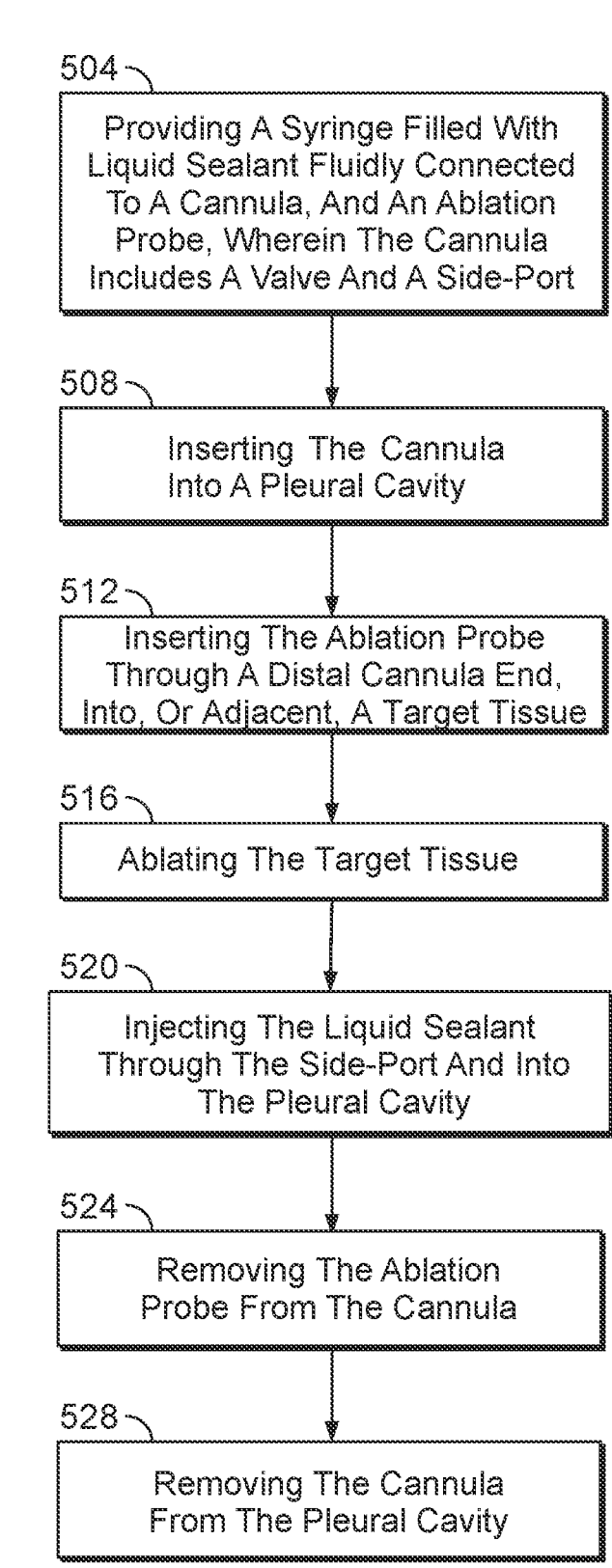

504

Providing A Syringe Filled With
Liquid Sealant Fluidly Connected
To A Cannula, And An Ablation
Probe, Wherein The Cannula
Includes A Valve And A Side-Port

508

Inserting The Cannula
Into A Pleural Cavity

512

Inserting The Ablation Probe
Through A Distal Cannula End,
Into, Or Adjacent, A Target Tissue

516

Ablating The Target Tissue

520

Injecting The Liquid Sealant
Through The Side-Port And Into
The Pleural Cavity

524

Removing The Ablation
Probe From The Cannula

528

Removing The Cannula
From The Pleural Cavity

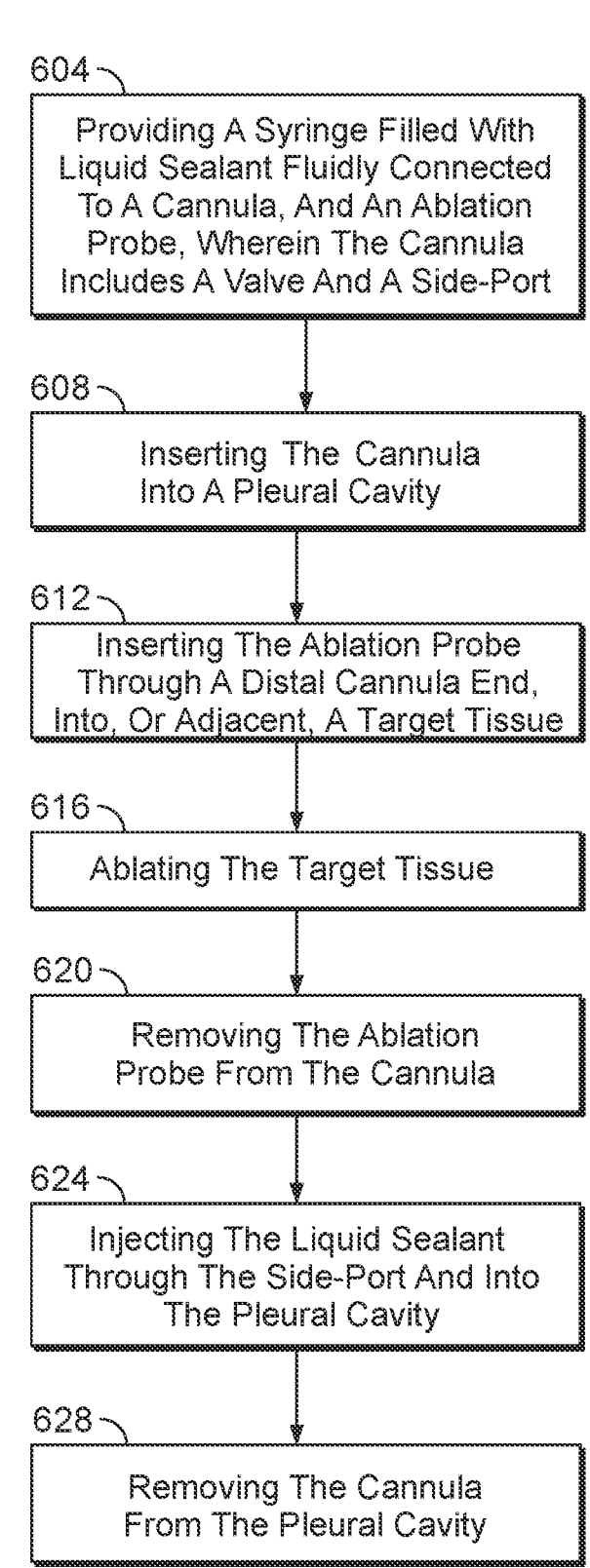

604

Providing A Syringe Filled With Liquid Sealant Fluidly Connected To A Cannula, And An Ablation Probe, Wherein The Cannula Includes A Valve And A Side-Port

608

Inserting The Cannula Into A Pleural Cavity

612

Inserting The Ablation Probe Through A Distal Cannula End, Into, Or Adjacent, A Target Tissue

616

Ablating The Target Tissue

620

Removing The Ablation Probe From The Cannula

624

Injecting The Liquid Sealant Through The Side-Port And Into The Pleural Cavity

628

Removing The Cannula From The Pleural Cavity

FIG. 6

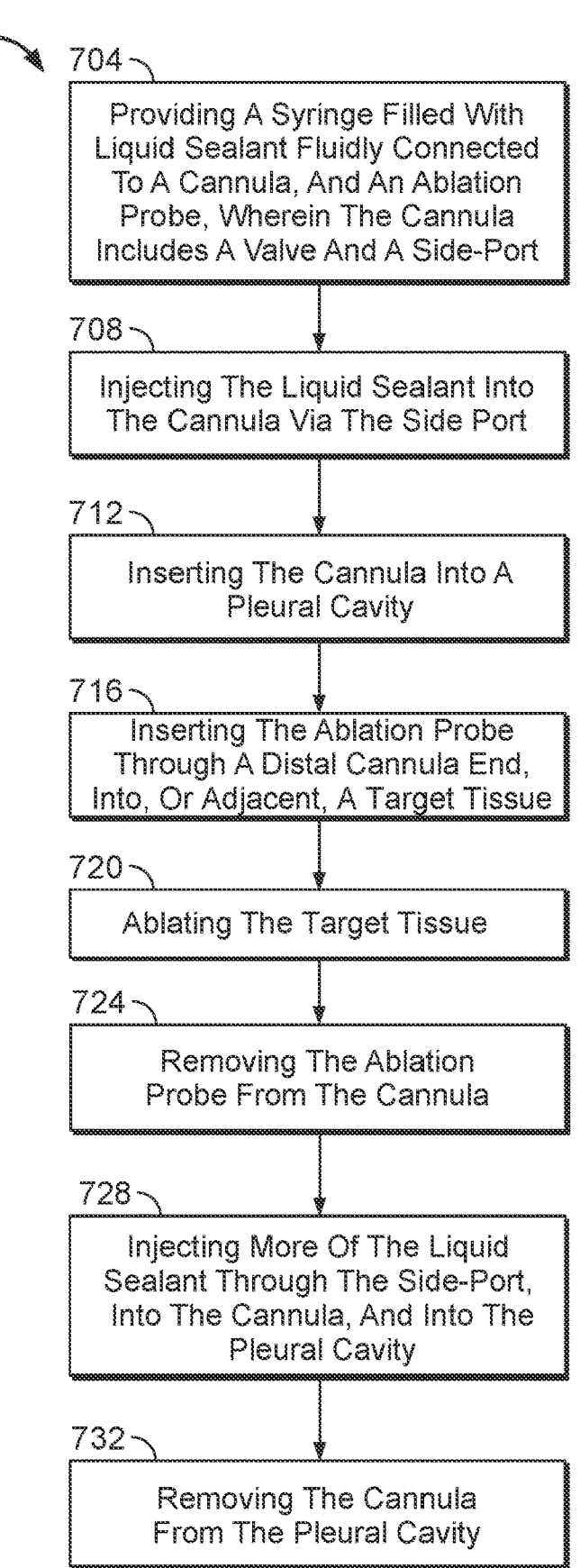

700

704

Providing A Syringe Filled With Liquid Sealant Fluidly Connected To A Cannula, And An Ablation Probe, Wherein The Cannula Includes A Valve And A Side-Port

708

Injecting The Liquid Sealant Into The Cannula Via The Side Port

712

Inserting The Cannula Into A Pleural Cavity

716

Inserting The Ablation Probe Through A Distal Cannula End, Into, Or Adjacent, A Target Tissue

720

Ablating The Target Tissue

724

Removing The Ablation Probe From The Cannula

728

Injecting More Of The Liquid Sealant Through The Side-Port, Into The Cannula, And Into The Pleural Cavity

732

Removing The Cannula From The Pleural Cavity

FIG. 7

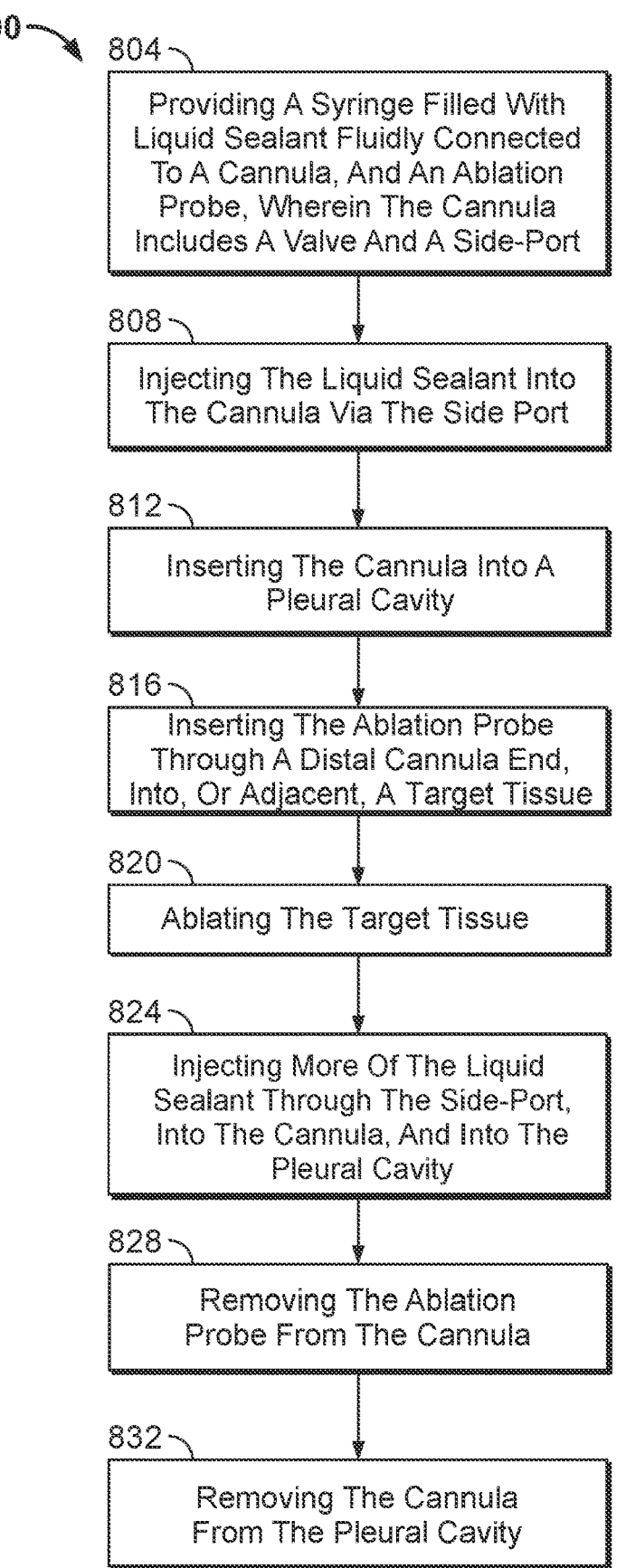

800

804
Providing A Syringe Filled With Liquid Sealant Fluidly Connected To A Cannula, And An Ablation Probe, Wherein The Cannula Includes A Valve And A Side-Port 808
Injecting The Liquid Sealant Into The Cannula Via The Side Port 812
Inserting The Cannula Into A Pleural Cavity 816
Inserting The Ablation Probe Through A Distal Cannula End, Into, Or Adjacent, A Target Tissue 820
Ablating The Target Tissue 824
Injecting More Of The Liquid Sealant Through The Side-Port, Into The Cannula, And Into The Pleural Cavity 828
Removing The Ablation Probe From The Cannula 832
Removing The Cannula From The Pleural Cavity

FIG. 8

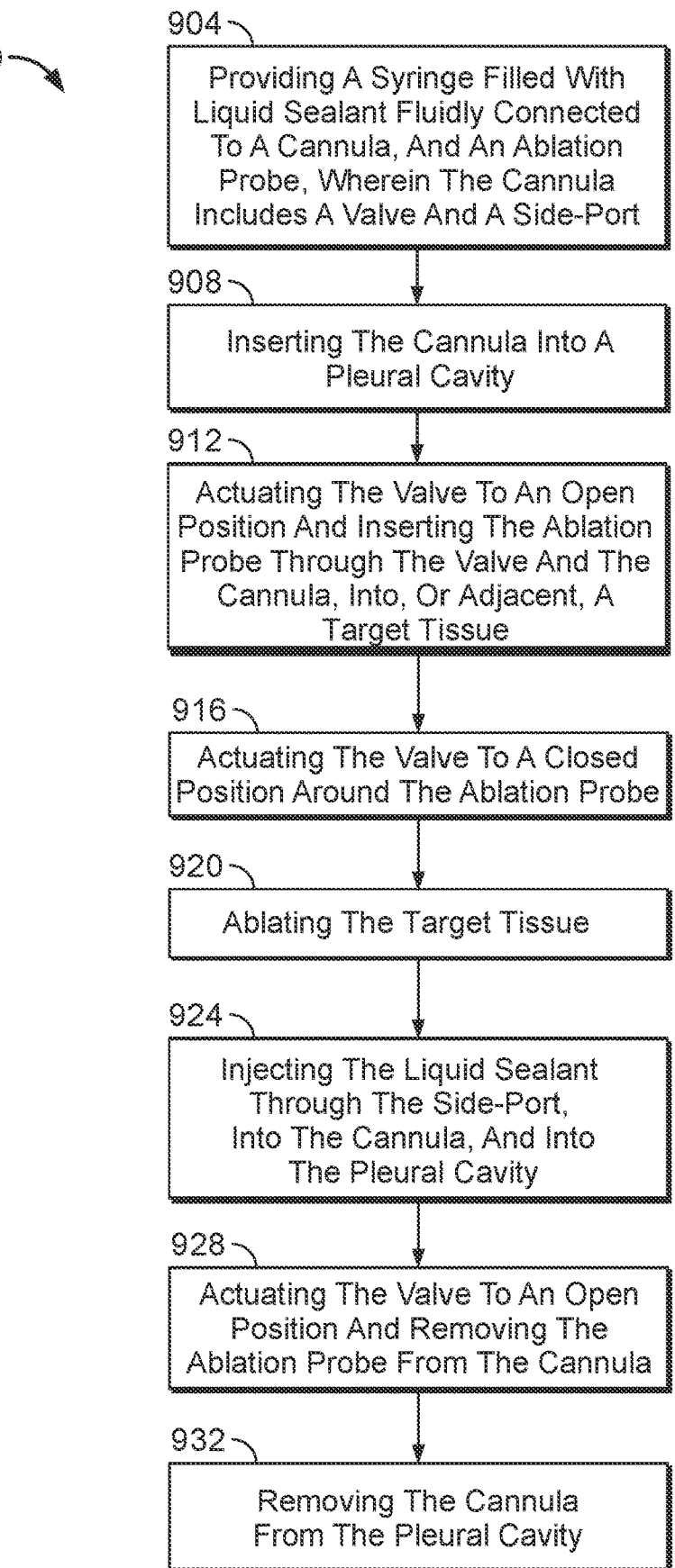

900

904
Providing A Syringe Filled With Liquid Sealant Fluidly Connected To A Cannula, And An Ablation Probe, Wherein The Cannula Includes A Valve And A Side-Port 908
Inserting The Cannula Into A Pleural Cavity 912
Actuating The Valve To An Open Position And Inserting The Ablation Probe Through The Valve And The Cannula, Into, Or Adjacent, A Target Tissue 916
Actuating The Valve To A Closed Position Around The Ablation Probe 920
Ablating The Target Tissue 924
Injecting The Liquid Sealant Through The Side-Port, Into The Cannula, And Into The Pleural Cavity 928
Actuating The Valve To An Open Position And Removing The Ablation Probe From The Cannula 932
Removing The Cannula From The Pleural Cavity

FIG. 9

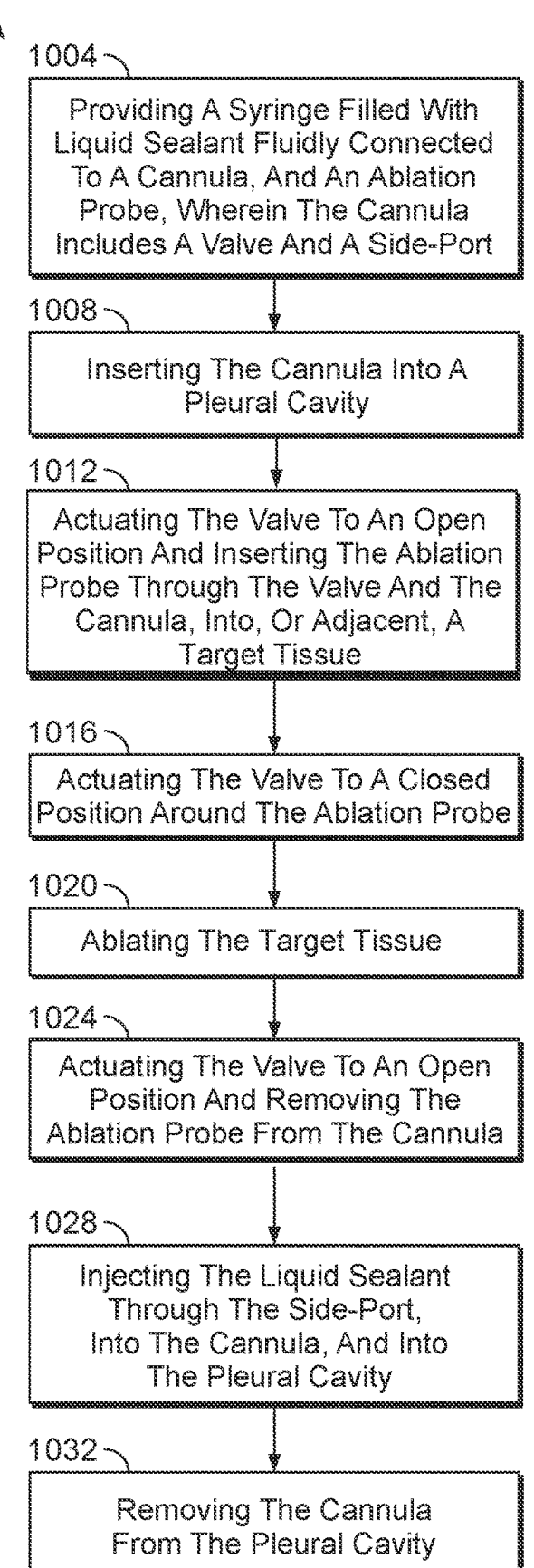

1000

1004
Providing A Syringe Filled With Liquid Sealant Fluidly Connected To A Cannula, And An Ablation Probe, Wherein The Cannula Includes A Valve And A Side-Port 1008
Inserting The Cannula Into A Pleural Cavity 1012
Actuating The Valve To An Open Position And Inserting The Ablation Probe Through The Valve And The Cannula, Into, Or Adjacent, A Target Tissue 1016
Actuating The Valve To A Closed Position Around The Ablation Probe 1020
Ablating The Target Tissue 1024
Actuating The Valve To An Open Position And Removing The Ablation Probe From The Cannula 1028
Injecting The Liquid Sealant Through The Side-Port, Into The Cannula, And Into The Pleural Cavity 1032
Removing The Cannula From The Pleural Cavity

FIG. 10

PERCUTANEOUS LUNG ABLATION CLOSURE DEVICE

BACKGROUND

Ablation is a minimally invasive procedure capable of treating and destroying tumors located in tissues such as the lung, liver, thyroid, and kidney. Patients who wish to avoid conventional surgery, or are too ill to undergo surgery due to preexisting conditions, may opt to treat their cancer using ablation. For many patients, the procedure causes minimal pain and has a very short recovery period.

Thermal ablation destroys cancer cells using either radiofrequency, microwaves, or cryoablation. During a thermal ablation procedure, one or more needles are inserted into or around a target tumor. The needles are then energized to create either intense heat or cold to ablate, or destroy, the cancerous cells.

The most common complication of a lung thermal ablation procedure is pneumothorax, reported at a rate of 12% to 19% in cryoablation procedures. Using more than one needle can further increase the rate of pneumothorax during thermal ablation procedures. Pneumothorax occurs when air leaks into the space between the lung and the chest wall, and can lead to the collapse of the lung. If the lung collapses, the patient must undergo a second procedure in which a small tube called a chest drain is inserted into the area of the pneumothorax to remove the air pocket.

During an ablation procedure, air may leak into the lung at any point in time through the cannula or through the hole in the tissue created by the cannula. Air is most likely to leak into the lung during insertion and removal of the cannula and/or ablation instrument. Accordingly, it would be desirable to have new instruments and procedures that reduce the likelihood of pneumothorax caused by thermal ablation procedures.

SUMMARY

The present disclosure provides systems and methods that overcome the aforementioned drawbacks. In accordance with some non-limiting examples of the disclosed subject matter, a method of reducing pneumothorax in a percutaneous lung procedure using a cannula having a lumen extending from a first opening to a second opening and having a third opening arranged along a length of the lumen is provided. The method comprises coupling a reservoir containing a liquid sealant to the third opening of the cannula. While the cannula is arranged within a subject such that the second opening of the lumen opens into a pleural cavity of the subject, injecting the liquid sealant from the reservoir into the lumen such that the liquid sealant flows out of the second opening of the cannula into the pleural cavity. The method further comprises withdrawing the cannula from the pleural cavity such that air is unable to infiltrate the pleural cavity by way of the liquid sealant.

In accordance with another non-limiting example of the disclosure, a method for ablating a lung tumor is provided. The method comprises providing a cannula having a housing including a proximal opening, a distal opening, and a side-port opening. The method further comprises coupling a reservoir filled with a liquid sealant to the side-port opening. The method further comprises inserting a distal end of the cannula percutaneously into a pleural cavity. The method further comprises inserting an ablation probe into the pleural cavity through the cannula. The method further comprises ablating lung tissue via the ablation probe. The method further comprises injecting the liquid sealant into the pleural cavity via the cannula. The method further comprises removing the ablation probe from the pleural cavity. The method further comprises removing the cannula from the pleural cavity.

In accordance with another non-limiting example of the disclosure, a percutaneous cannula device kit is provided. The percutaneous device kit comprises, a reservoir containing a liquid sealant, and a cannula device. The cannula device comprise a housing including a distal housing opening and a proximal housing opening connected by a housing lumen. The cannula device further comprises a cannula to insert through the distal housing opening. The cannula includes a proximal cannula opening and a distal cannula opening connected by a cannula lumen. The housing or cannula lumen includes a side-port opening to fluidically couple the reservoir to the housing or cannula lumen.

BRIEF DESCRIPTIONS OF THE DRAWINGS

FIG. 5 is a method for ablating a tumor within a patient, in accordance with some non-limiting examples of the disclosed subject matter.

FIG. 6 is a method for ablating a tumor within a patient, in accordance with some non-limiting examples of the disclosed subject matter.

FIG. 7 is a method for ablating a tumor within a patient, in accordance with some non-limiting examples of the disclosed subject matter.

FIG. 8 is a method for ablating a tumor within a patient, in accordance with some non-limiting examples of the disclosed subject matter.

FIG. 9 is a method for ablating a tumor within a patient, in accordance with some non-limiting examples of the disclosed subject matter.

FIG. 10 is a method for ablating a tumor within a patient, in accordance with some non-limiting examples of the disclosed subject matter.

DETAILED DESCRIPTION

Figure 1:
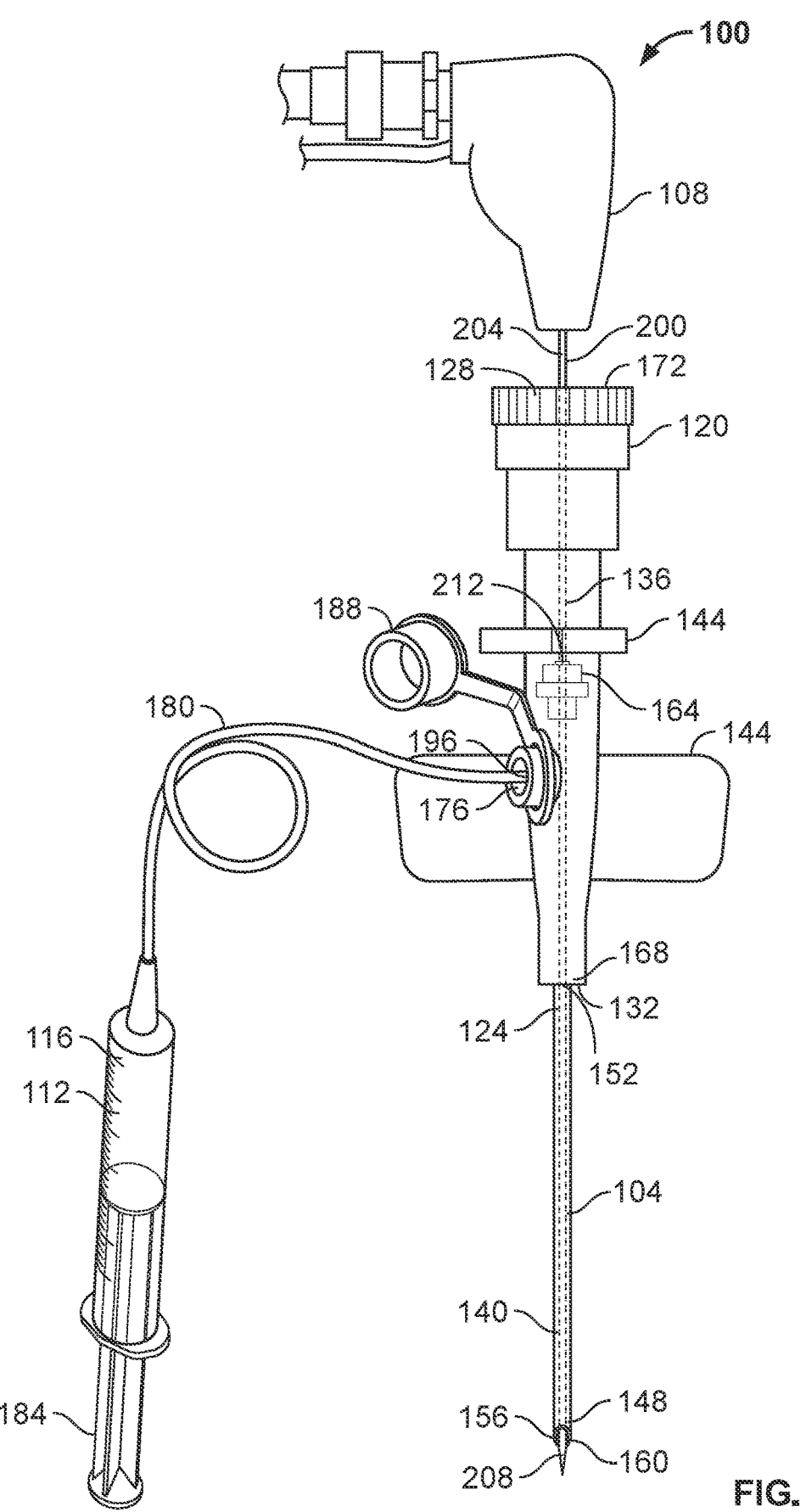
FIG. 1 is a side view of an ablation device, in accordance with some non-limiting examples of the disclosed subject matter.

In accordance with various non-limiting examples, mechanisms and tools (which can, for example, include systems, methods, and media) for performing thermal ablation procedures are described herein. In accordance with various non-limiting examples, an improved ablation device can reduce the rate of pneumothorax caused by lung ablation procedures.

In some non-limiting examples, the ablation device can provide an improved instrument for reducing the likelihood of pneumothorax during or after ablation procedures. Additionally or alternately, the ablation device may include a cannula that can be used in other treatments requiring the percutaneous insertion of a foreign object into the lung, such as biopsies. As will be described, the ablation device utilizes the injection of a liquid sealant into the pleural cavity to reduce the likelihood of air leakage into the pleural cavity where it may cause pneumothorax during or after the ablation procedure. The non-limiting example is provided to illustrate the functionality and methods of use for the improved ablation device. The below description is but an example and should not limit the scope of the present disclosure.

The ablation device includes a cannula, an ablation probe, and a syringe filled with liquid sealant, in fluid communication with the cannula. The cannula is configured to be inserted into a patient's tissue, to access a target tissue for the ablation probe. The syringe is configured to provide a liquid sealant through the cannula to an internal volume of the patient's body (e.g., the pleural cavity) to reduce the likelihood for air leakage into the patient's body (e.g., air leakage into the pleural cavity where it would result in pneumothorax). The cannula is configured to provide a pathway for the ablation probe to access and ablate the target tissue.

In some non-limiting examples, the ablation device includes a valve or seal disposed within the cannula. The valve is configured to restrict fluid flow through a proximal opening, an opening closest to the operator. In some non-limiting examples, the valve receives the ablation probe and forms a fluid tight seal around the ablation probe.

In some non-limiting examples, the cannula includes a side port to fluidly connect the syringe to a central lumen of the cannula. The syringe is configured to inject the liquid sealant into the lumen of the cannula to reduce the likelihood of pneumothorax caused following the ablation procedure. In some non-limiting examples, the liquid sealant is injected into the cannula, and the patient's tissue during insertion or removal of the cannula or the ablation probe. In some non-limiting examples, the liquid sealant is continuously injected into the tissue during the ablation procedure. In some non-limiting examples, the liquid sealant is manually injected by an operator at the discretion of the operator. In some non-limiting examples, the liquid sealant is injected by a robot or machine (e.g., during a robot-assisted procedure).

Referring to FIG. 1, an ablation device 100 for ablating tumors within a patient is illustrated. The ablation device 100 may be used by itself or in conjunction with one or more similar ablation devices during an ablation procedure. The ablation device 100 includes a cannula 104, an ablation probe 108, and a syringe 112 (or other reservoir) filled with liquid sealant 116 in fluid communication with the cannula 104.

Referring still to FIG. 1, the ablation device 100 may include a housing 120 coupled to a proximal cannula end 124. The housing 120 may include a proximal housing opening 128 and a distal housing opening 132, connected by a housing lumen 136. A portion of the proximal cannula end 124 may be received within the distal housing opening 132, and may be retained within the housing lumen 136. A center housing axis may be colinear with a center cannula axis, aligning the housing lumen 136 with a cannula lumen 140.

The housing 120 may include a variable cylindrical shape with a variable outer diameter. The outer diameter of the housing 120 may taper towards the distal housing opening 132. The outer diameter of the housing 120 may be greater than an outer diameter of the cannula 104, providing an easier handhold of the ablation device 100 for a user. The housing 120 may further include projections 144, extending radially from housing 120 to assist the user in gripping the ablation device 100. The projections 144 (e.g., wings, ridges, knobs, etc.) may be located anywhere along the housing 120.

The cannula 104 is received into the housing lumen 136 of the housing 120. In some embodiments, the housing 120 is separate from the cannula 104 and is coupled to the cannula 104 via a threading, friction fit, over molding, adhesive, Luer taper, Tuohy Borst adapter, or any other suitable coupling arrangement. In some embodiments, the housing 120 and the cannula 104 are integral, or are manufactured as a unitary piece.

The cannula 104 extends between a proximal cannula end 124 and a distal cannula end 148. The cannula 104 includes a proximal cannula opening 152 in the proximal cannula end 124 and a distal cannula opening 156 in the distal cannula end 148. In some embodiments, the cannula 104 may taper toward the distal cannula end 148. In some embodiments, the cannula 104 may include a distal cannula end 148 that is round, flat, hooked, or any other suitable shape.

Referring still to FIG. 1, the cannula 104 is illustrated as a substantially straight cylinder, extending from the proximal cannula end 124 to the distal cannula end 148. In some embodiments, the cannula 104 may include one or more inflection points. At the one or more inflection points, the cannula 104 may include an arcuate bend or arch to allow a user to reach a tumor located behind a rib, or in another hard-to-reach location. The bend may have an angle ranging from about 5 to about 45 degrees, or about 10 to about 30 degrees, or about 10 to about 20 degrees. In some embodiments, the shape of the cannula 104 may be arcuate or arched along an entire length of the cannula 104.

Referring still to FIG. 1, the cannula 104 may be formed as a hollow needle that includes the cannula lumen 140 centrally disposed within the cannula 104 and extending from the proximal cannula opening 152 to the distal cannula opening 156. In some embodiments, the cannula lumen 140 extends only partially from the distal cannula end 148 to the proximal cannula end 124. In some embodiments, a diameter of the cannula lumen 140 may change along the length of the cannula 104. For example, the diameter of the cannula lumen 140 may taper toward the distal cannula end 148 or toward the proximal cannula end 124.

Referring still to FIG. 1, the distal cannula end 148 is configured to penetrate a patient's tissue. In some embodiments, the distal cannula end 148 includes a cutting portion 160. The cutting portion 160 may be angled relative to a central axis of the cannula 104. The angled geometry of the cutting portion 160 may be configured to prevent tissue from entering the cannula lumen 140 while the cutting portion 160 cuts into tissue by piercing the tissue and gradually pushing the tissue apart, similar to the function of a hypodermic needle.

The cannula lumen 140 includes a valve 164, or seal, that may be disposed anywhere along the cannula lumen 140. In some embodiments, the valve 164 is configured to restrict fluid communication between the proximal cannula opening 152 and the distal cannula opening 156. In some embodiments, the valve 164 may be positioned in the housing lumen 136 proximate to the proximal cannula end 124 to restrict fluid flow between the cannula 104 and the housing 120. In some embodiments, the valve 164 may be positioned anywhere within the housing lumen 136 to restrict fluid flow between the housing 120 (and/or cannula 104) and an exterior environment.

In some embodiments, the valve 164 is separate from the housing 120 and cannula 104. In some embodiments, the valve 164 may be coupled to a distal housing end 168 or a proximal housing end 172. In some embodiments, the valve 164 may be coupled to the proximal cannula end 124 between the housing 120 and the cannula 104. In some embodiments, the valve 164 may be coupled to the housing 120 or cannula 104 via a threading, friction fit, over molding, adhesive, Tuohy Borst adapter, Luer taper, or other suitable coupling means.

In some embodiments, the valve 164 may be a check valve or a one-way valve, configured to either restrict fluid flow within the ablation device 100 in a proximal to distal direction, or in a distal to proximal direction. In some embodiments the valve 164 may be a relief valve, configured to allow fluid to flow within the ablation device 100 in either a proximal to distal direction, or in a distal to proximal direction, when pressure within the cannula lumen 140 exceeds a set pressure. In some embodiments, the valve 164 may be an on-off valve configured to allow fluid to flow within the ablation device 100 in either a proximal to distal direction, or in a distal to proximal direction when actuated to an on position. The on-off valve may be actuated between the on position and an off position via the projections 144 on the housing 120 or on the cannula 104. In some embodiments, the projections 144 may include a component that is rotatable around the cannula center axis. In some embodiments, the projections 144 include a component that is translated along the length of the cannula 104 or housing 120, in a proximal to distal direction or in a distal to proximal direction. In some embodiments, the projection 144 is a rotatable knob extending from the housing 120 or cannula 104.

The cannula 104 may include a side-port opening 176, that allows for fluid communication with the cannula lumen 140. In some embodiments, the side-port opening 176 is located to allow for fluid communication with the housing lumen 136. The side-port opening 176 may be disposed anywhere along the length of the cannula 104 or housing 120. In some embodiments, the side-port opening 176 is disposed between the distal cannula end 148 and the valve 164 in order to supply fluid through the cannula lumen 140 to the distal cannula end 148 of the cannula 104, such that the fluid may then flow out of the distal cannula opening 156.

Figure 2:
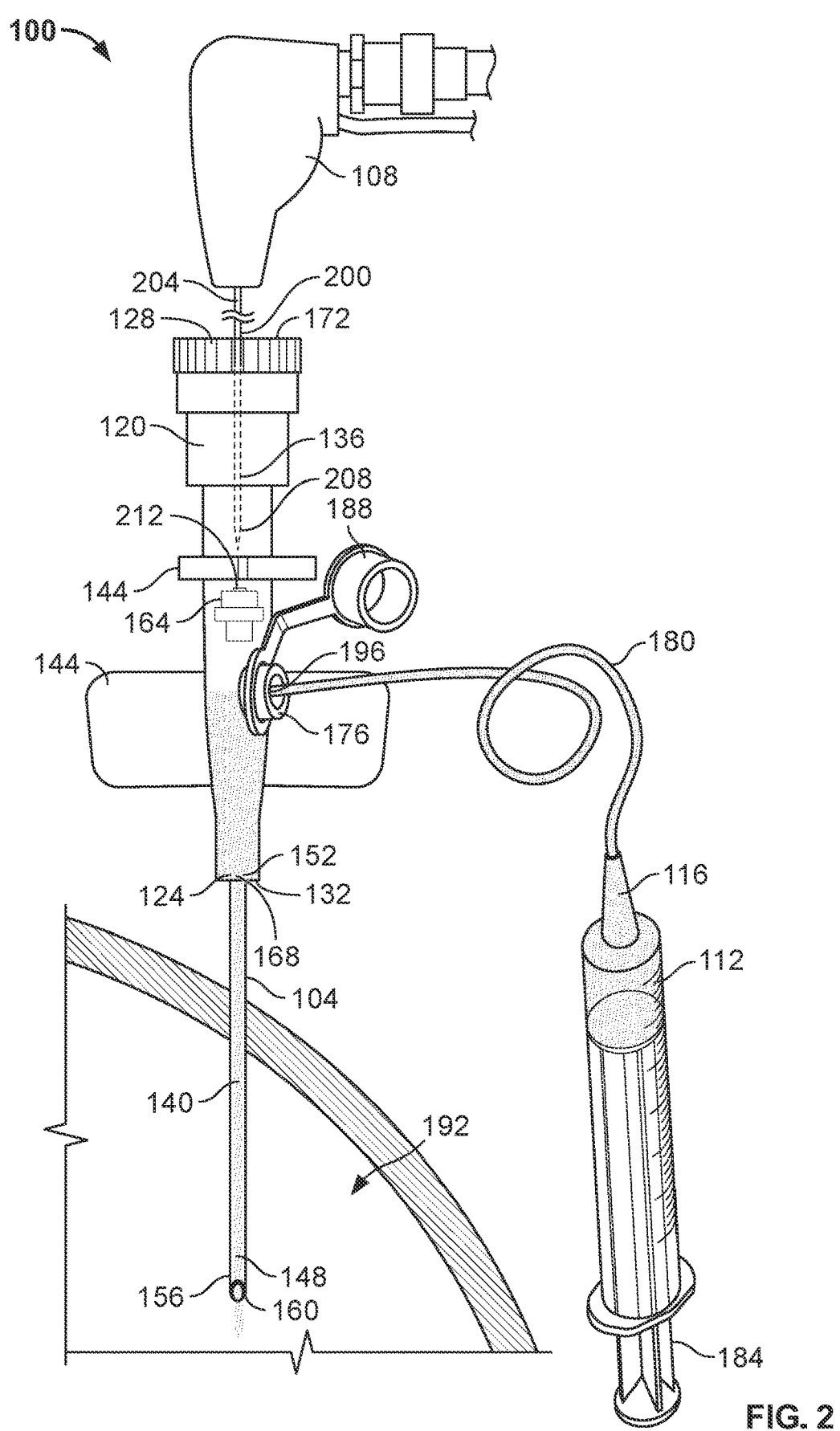
FIG. 2 is a view of the device of FIG. 1, inserted into a patient's pleural cavity.

As illustrated in FIG. 2, the side-port opening 176 may be in fluid communication with the syringe 112 via a tube 180. The syringe 112 may hold the liquid sealant 116, such as, saline, blood, plasma, water, etc. In some embodiments, the liquid sealant 116 may be blood extracted from the patient, or may be blood taken from a donor. An operator of the ablation device 100 may depress a plunger 184 on the syringe 112 to force the liquid sealant 116 through the tube 180 into the cannula lumen 140. The liquid sealant 116 may then flow through the cannula lumen 140 and out of the distal cannula opening 156. In some embodiments, the side-port opening 176 is in fluid communication with a pump, an automated syringe, or other machine capable of forcing the liquid sealant 116 through the side-port opening 176 from a reservoir of the liquid sealant 116. When not in use, the side-port opening 176 may be coupled to a cap 188 to prevent leakage of fluid or air, into or out of the cannula lumen 140.

The liquid sealant 116 is configured to reduce the risk of pneumothorax caused by, or following, the ablation procedure. As described above, air may leak into the pleural cavity 192 during the ablation procedure, or after withdrawing the ablation probe 108 and/or cannula 104 from the patient. Air may leak into the pleural cavity 192 through the cannula 104, or the hole created by the cannula 104 in the parietal pleura (i.e., the outer surface of the pleural cavity 192) at least during the insertion and removal of the cannula 104 and ablation probe 108. The present device fills the cannula 104 with the liquid sealant 116 to reduce the amount of air present in the cannula 104, that could potentially leak into the pleural cavity 192 where it would cause pneumothorax. With liquid sealant 116 present in the cannula 104, the liquid sealant 116 effectively creates a plug or seal in the pleural cavity 192 (or the hole in the parietal pleura) and in the cannula 104, ensuring air cannot enter the pleural cavity 192.

In some embodiments, the liquid sealant 116 is injected into the cannula 104 prior to or during the insertion of the cannula 104 into the pleural cavity 192. In some embodiments, the liquid sealant 116 is injected into the pleural cavity 192 prior to or during the insertion of the ablation probe 108 into the pleural cavity 192. In some embodiments, the liquid sealant 116 is injected into the cannula 104 and into the pleural cavity 192 prior to or during the removal of the cannula 104 from the pleural cavity 192. Injecting the liquid sealant 116 into the pleural cavity 192 during the removal of the cannula 104 effectively fills the hole created by the cannula 104 in the parietal pleura, ensuring air cannot leak into the pleural cavity 192. In some embodiments, the liquid sealant 116 is injected into the pleural cavity 192 prior to or during the removal of the ablation probe 108 from the pleural cavity 192. In some embodiments, the liquid sealant 116 is injected into the cannula 104 during the entire ablation procedure.

As an example, FIG. 2 illustrates the injection of the liquid sealant 116 into the cannula 104 and into the pleural cavity 192 either before the insertion of the ablation probe 108, or after the removal of the ablation probe 108. As illustrated, no air enters the pleural cavity 192, as the liquid sealant 116 forms a seal in the pleural cavity 192 (e.g., in the parietal pleura) and in the cannula 104

In some embodiments, the side-port opening 176 may include a side-port valve 196. The side-port valve 196 is configured to restrict fluid communication between the tube 180 and the cannula lumen 140 or the housing lumen 136. The side-port valve 196 may be located in the cannula 104, the housing 120, or the tube 180. In some embodiments, the side-port valve 196 may be a check valve or one way valve, configured to either restrict fluid flow from the tube 180 into the cannula lumen 140, or from the cannula lumen 140 into the tube 180. In some embodiments the side-port valve 196 may be a relief valve, configured to allow fluid to flow from the tube 180 into the cannula lumen 140, or from the cannula lumen 140 into the tube 180, when pressure within either the tube 180 or the cannula lumen 140 exceeds a set pressure. In some embodiments, the side-port valve 196 may be an on-off valve configured to allow fluid to flow from the tube 180 into the cannula lumen 140, or from the cannula lumen 140 into the tube 180, when actuated to an on position. The side-port valve 196 may be coupled to the ablation device

100 via a threading, friction fit, over molding, adhesive, Tuohy Borst adapter, Luer taper, or other suitable coupling means.

As will be further described, the cannula 104 may be configured for use with an ablation system, such as, for example a thermal ablation system (e.g., radiofrequency ablation, microwave ablation, cryoablation, etc.). The cannula 104 may further be configured for use with lung biopsy procedures, which include another type of percutaneous lung procedure associated with a high risk for pneumothorax. In these instances, the cannula lumen 140 may receive a biopsy needle rather than the ablation probe 108. More generally, the cannula lumen 140 may receive surgical tools other than the ablation probe 108 or a biopsy needle depending on the percutaneous lung procedure being performed on the subject.

Referring to FIGS. 3A-4C, the cannula lumen 140 of the cannula 104 may be configured to receive a shaft 200 of the ablation probe 108. The shaft 200 is received through the proximal cannula opening 152 into the cannula lumen 140. In some embodiments, a portion of a proximal shaft end 204 is retained within the housing lumen 136 while a distal shaft end 208 extends into the cannula lumen 140. Referring to FIGS. 3C and 4A, during a procedure, the distal shaft end 208 may be configured to extend past the distal cannula end 148 of the cannula 104. The distal shaft end 208 extends into the tissue of the patient, and is configured to ablate the target tissue.

Still referring to FIGS. 3A-4C, the shaft 200 of the ablation probe 108 is inserted into the cannula lumen 140, and through the valve 164. In some embodiments, the valve 164 may be configured to receive the shaft 200, while forming a fluid tight seal. The valve 164 may include an aperture 212 for receiving the shaft 200. In some embodiments, the aperture 212 may be configured to increase or decrease in diameter to receive, retain, and release the shaft 200. The aperture 212 may be actuated to decrease the diameter of the aperture to form a fluid tight seal with the shaft 200. The aperture 212 may decrease in diameter via rotation or translation of the radial projections located on the cannula 104 or housing 120. In some embodiments, the valve 164 may include the aperture 212 that has a diameter similar to the diameter of the shaft 200, to create a friction seal with the shaft 200, when the shaft 200 is inserted through the valve 164. In some embodiments, the aperture 212 may be threaded, configured to receive a threading on an exterior surface of the shaft 200. In some embodiments, the aperture 212 includes leaflets configured to deform to accept the shaft 200 and create a fluid tight seal.

Figures 3A, 3B, 3C:
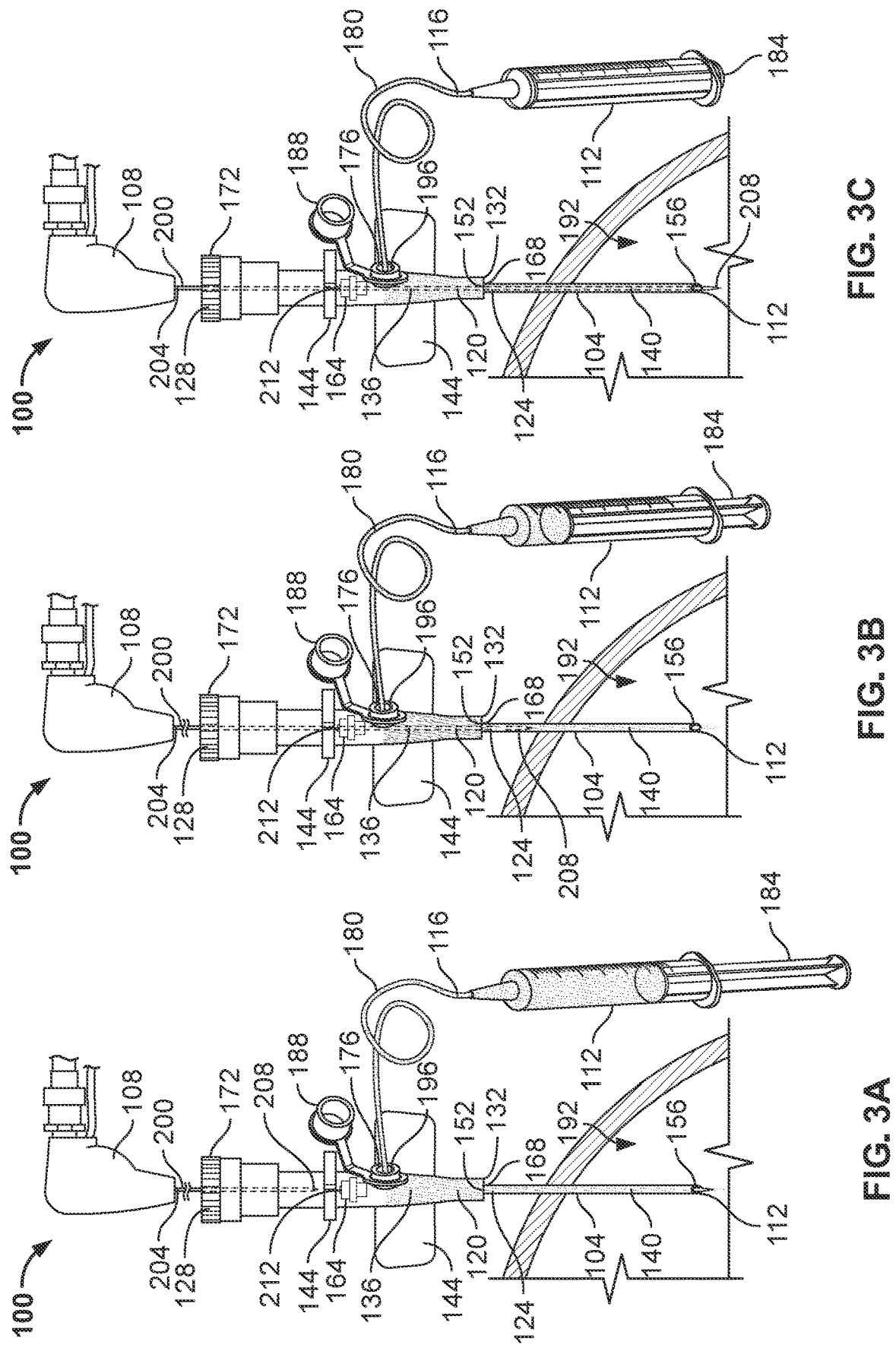
FIG. 3A is a view of the device of FIG. 1, inserted into a pleural cavity, injecting a liquid sealant into the pleural cavity.
FIG. 3B is a view of the device of FIG. 1, inserted into a pleural cavity, inserting an ablation probe into the pleural cavity.
FIG. 3C is a view of the device of FIG. 1, inserted into a pleural cavity, ablating a target tissue in the patient's lung.

Referring to FIGS. 3A-3C, a non-limiting example process for the insertion of the ablation probe 108 into the patient's pleural cavity 192 is depicted. As described above, the liquid sealant 116 may be injected into the pleural cavity 192 prior to the insertion of the ablation probe 108. In the illustrated example, the liquid sealant 116 may be continually injected into the pleural cavity 192 until the distal shaft end 208 extends into the pleural cavity 192. During the ablation of the target tissue(s) in the patient's lung, the liquid sealant 116 may or may not be continuously injected into the pleural cavity 192.

Figures 4A, 4B, 4C:
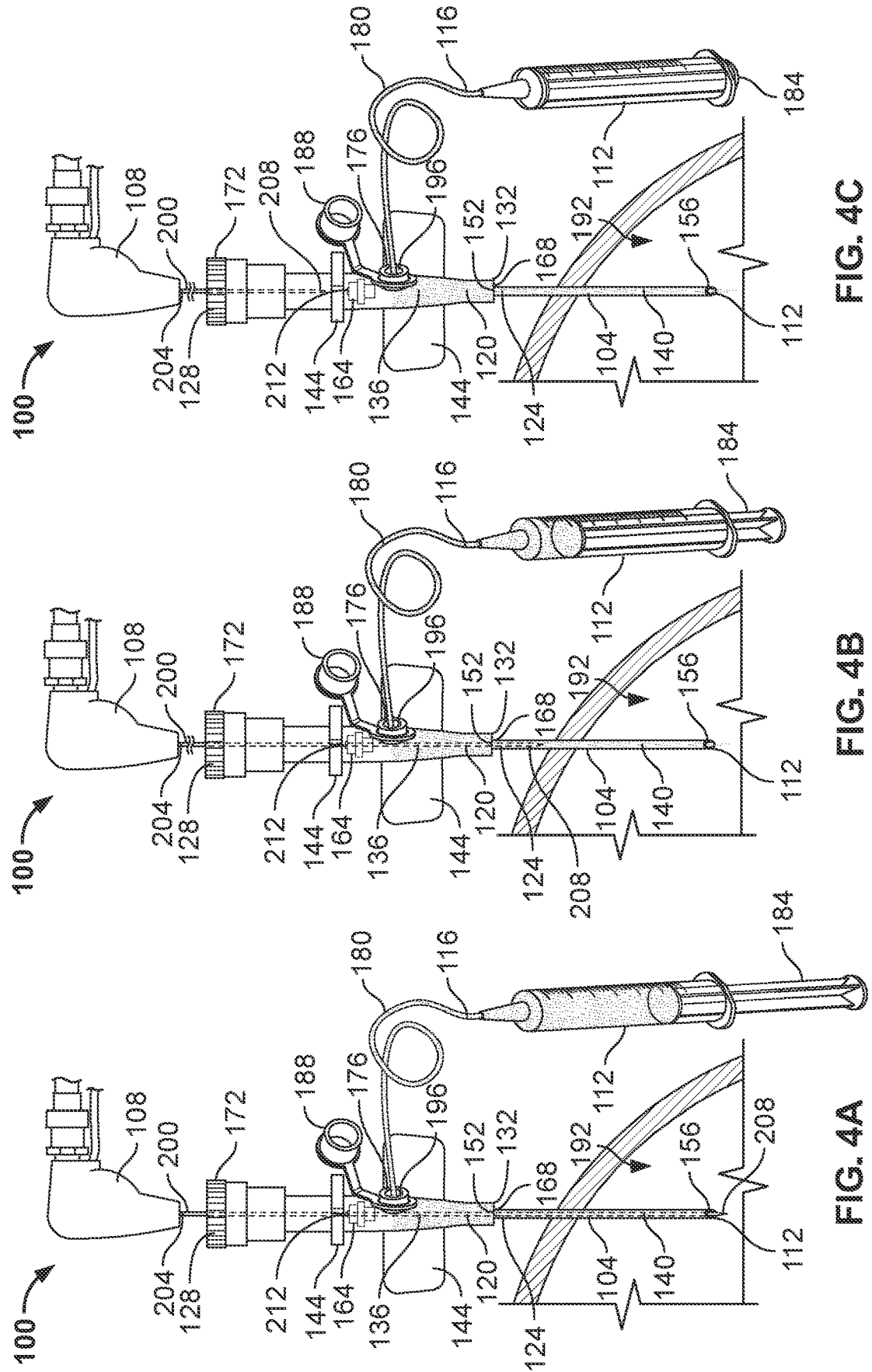
FIG. 4A is a view of the device of FIG. 1, inserted into a pleural cavity, ablating a target tissue in the patient's lung.
FIG. 4B is a view of the device of FIG. 1, inserted into a pleural cavity, beginning to withdraw an ablation probe from the pleural cavity.
FIG. 4C is a view of the device of FIG. 1, inserted into a pleural cavity, prior to the withdrawal of a cannula in the pleural cavity.

Referring to FIGS. 4A-4C, a non-limiting example process for the removal of the ablation probe 108 from the patient's pleural cavity 192 is depicted. As described above, the liquid sealant 116 may be injected into the pleural cavity 192 prior to the removal of the ablation probe 108. As illustrated the liquid sealant 116 is configured to flow around the shaft 200 of the ablation probe 108 into the pleural cavity

192. In the illustrated example, the liquid sealant 116 is injected into the pleural cavity 192 prior to the removal of the ablation probe 108. The ablation probe 108 is then removed, leaving no gaps to allow for air to leak into the pleural cavity 192 through the cannula 104.

Referring now to FIG. 5, a method 500 is illustrated for an ablation procedure, which may include fewer or more steps than depicted. In some embodiments, the following steps are performed in any order. In some embodiments, two or more of the following steps are performed simultaneously. At a first step 504, the method 500 includes providing a syringe filled with liquid sealant fluidly connected to a cannula, and an ablation probe, wherein the cannula includes a valve and a side-port. At a second step 508, the method 500 includes inserting the cannula into a pleural cavity (e.g., through the parietal pleura and into the plural cavity). At a third step 512, the method 500 includes inserting the ablation probe through a distal cannula end, into, or adjacent, a target tissue (e.g., lung tissue). At a fourth step 516, the method 500 includes ablating the target tissue. At a fifth 520 step, the method 500 includes injecting the liquid sealant through the side-port and into the pleural cavity. At a sixth step 524, the method 500 includes removing the ablation probe from the cannula. At a seventh step 528, the method 500 includes removing the cannula from the pleural cavity.

Referring now to FIG. 6, a method 600 is illustrated for an ablation procedure, which may include fewer or more steps than depicted. In some embodiments, the following steps are performed in any order. In some embodiments, two or more of the following steps are performed simultaneously. At a first step 604, the method 600 includes providing a syringe filled with liquid sealant fluidly connected to a cannula, and an ablation probe, wherein the cannula includes a valve and a side-port. At a second step 608, the method 600 includes inserting the cannula into a pleural cavity (e.g., through the parietal pleura and into the plural cavity). At a third step 612, the method 600 includes inserting the ablation probe through a distal cannula end, into, or adjacent, a target tissue (e.g., lung tissue). At a fourth step 616, the method 600 includes ablating the target tissue. At a fifth step 620, the method 600 includes removing the ablation probe from the cannula. At a sixth 624 step, the method 600 includes injecting the liquid sealant through the side-port and into the pleural cavity. At a seventh step 628, the method 600 includes removing the cannula from the pleural cavity.

Referring now to FIG. 7, a method 700 is illustrated for an ablation procedure, which may include fewer or more steps than depicted. In some embodiments, the following steps are performed in any order. In some embodiments, two or more of the following steps are performed simultaneously. At a first step 704, the method 700 includes providing a syringe filled with liquid sealant fluidly connected to a cannula, and an ablation probe, wherein the cannula includes a valve and a side-port. At a second step 708, the method 700 includes injecting the liquid sealant into the cannula via the side port. At a third step 712, the method 700 includes inserting the cannula into a pleural cavity (e.g., through the parietal pleura and into the plural cavity). At a fourth step 716, the method 700 includes inserting the ablation probe through a distal cannula end, into, or adjacent, a target tissue (e.g., lung tissue). At a fifth step 720, the method 700 includes ablating the target tissue. At a sixth step 724, the method 700 includes removing the ablation probe from the cannula. At a seventh 728 step, the method 700 includes injecting more of the liquid sealant through the side-port, into the cannula, and into the pleural cavity. At an eighth step 732, the method 700 includes removing the cannula from the pleural cavity.

Referring now to FIG. 8, a method 800 is illustrated for an ablation procedure, which may include fewer or more steps than depicted. In some embodiments, the following steps are performed in any order. In some embodiments, two or more of the following steps are performed simultaneously. At a first step 804, the method 800 includes providing a syringe filled with liquid sealant and fluidly connected to a cannula, and an ablation probe, wherein the cannula includes a valve and a side-port. At a second step 808, the method 800 includes injecting the liquid sealant into the cannula via the side port. At a third step 812, the method 800 includes inserting the cannula into a pleural cavity (e.g., through the parietal pleura and into the plural cavity). At a fourth step 816, the method 800 includes inserting the ablation probe through a cannula distal end, into, or adjacent, a target tissue (e.g., lung tissue). At a fifth step 820, the method 800 includes ablating the target tissue. At a sixth step 824, the method 800 includes injecting more of the liquid sealant through the side-port, into the cannula, and into the pleural cavity. At a seventh 828 step, the method 800 includes removing the ablation probe from the cannula. At an eighth step 832, the method 800 includes removing the cannula from the pleural cavity.

As illustrated in FIGS. 7 and 8, injecting liquid sealant into the side-port opening 176, to fill or partially fill the cannula 104 reduces the amount of air/gas within the cannula prior to insertion of the cannula 104. By including the liquid sealant in the cannula 104 prior to the insertion of the cannula 104 into the pleural cavity (e.g., through the parietal pleura and into the plural cavity) 192, the methods reduce the risk for pneumothorax, as it reduces the possibility for air to be introduced into the chest cavity during the procedure.

Referring now to FIG. 9, a method 900 is illustrated for an ablation procedure, which may include fewer or more steps than depicted. In some embodiments, the following steps are performed in any order. In some embodiments, two or more of the following steps are performed simultaneously. At a first step 904, the method 900 includes providing a syringe filled with liquid sealant fluidly connected to a cannula, and an ablation probe, wherein the cannula includes a valve and a side-port. At a second step 908, the method 900 includes inserting the cannula into a pleural cavity (e.g., through the parietal pleura and into the plural cavity). At a third step 912, the method 900 includes actuating the valve to an open position and inserting the ablation probe through the valve and the cannula, into, or adjacent, a target tissue (e.g., lung tissue). At a fourth step 916, the method 900 includes actuating the valve to a closed position around the ablation probe. At a fifth step 920, the method 900 includes ablating the target tissue. At a sixth step 924, the method 900 includes injecting the liquid sealant through the side-port, into the cannula, and into the pleural cavity. At a seventh 928 step, the method 900 includes actuating the valve to an open position and removing the ablation probe from the cannula. At an eighth step 932, the method 900 includes removing the cannula from the pleural cavity.

Referring now to FIG. 10, a method 1000 is illustrated for an ablation procedure, which may include fewer or more steps than depicted. In some embodiments, the following steps are performed in any order. In some embodiments, two or more of the following steps are performed simultaneously. At a first step 1004, the method 1000 includes providing a syringe filled with liquid sealant fluidly connected to a cannula, and an ablation probe, wherein the cannula includes a valve and a side-port. At a second step 1008, the method 1000 includes inserting the cannula into a pleural cavity (e.g., through the parietal pleura and into the plural cavity). At a third step 1012, the method 1000 includes actuating the valve to an open position and inserting the ablation probe through the valve and the cannula, into, or adjacent, a target tissue (e.g., lung tissue). At a fourth step 1016, the method 1000 includes actuating the valve to a closed position around the ablation probe. At a fifth step 1020, the method 1000 includes ablating the target tissue. At a sixth step 1024, the method 1000 includes actuating the valve to an open position and removing the ablation probe from the cannula. At a seventh 1028 step, the method 1000 includes injecting the liquid sealant through the side-port, into the cannula, and into the pleural cavity. At an eighth step 1032, the method 1000 includes removing the cannula from the pleural cavity.

As illustrated in FIGS. 5-10, the liquid sealant 116 is injected into the cannula 104 prior to or during the removal of the ablation probe 108 and/or cannula 104. Injecting the liquid sealant 116 into the pleural cavity 192 during or prior to the removal of the ablation probe 108 and/or the cannula 104, fills the empty space created in the pleural cavity 192 created by the insertion of the cannula 104. By filling the empty space with the liquid sealant 116, the risk for pneumothorax decreases, as the liquid sealant 116 reduces the possibility for air to leak into the chest cavity while the ablation probe 108 and/or cannula 104 are removed.

As used herein, unless otherwise limited or defined, "integral" and derivatives thereof (e.g., "integrally") describe elements that are manufactured as a single piece without fasteners, adhesive, or the like to secure separate components together. For example, an element stamped, cast, or otherwise molded as a single-piece component from a single piece of sheet metal or using a single mold, without rivets, screws, or adhesive to hold separately formed pieces together is an integral (and integrally formed) element. In contrast, an element formed from multiple pieces that are separately formed initially then later connected together, is not an integral (or integrally formed) element.

Although the invention has been described and illustrated in the foregoing illustrative non-limiting examples, it is understood that the present disclosure has been made only by way of example, and that numerous changes in the details of implementation of the invention can be made without departing from the spirit and scope of the invention, which is limited only by the claims that follow. Features of the disclosed non-limiting examples can be combined and rearranged in various ways.

What is claimed is:

1. A method of reducing pneumothorax in a percutaneous lung procedure using a cannula having a lumen extending from a first opening to a second opening and having a third opening arranged along a length of the lumen, the method comprising:

coupling a reservoir containing a liquid sealant to the third opening of the cannula;

before the cannula is arranged within a subject, injecting the liquid sealant from the reservoir into the lumen to seal the lumen and prevent the flow of air into the lung of the subject via the cannula when the cannula is introduced into the lung of the subject;

while the cannula is arranged within the subject such that the second opening of the lumen opens into a pleural cavity of the subject, injecting the liquid sealant from the lumen out of the second opening of the cannula and into the pleural cavity; and withdrawing the cannula from the pleural cavity such that air is unable to infiltrate the pleural cavity by way of the liquid sealant.

2. The method of claim 1, wherein the cannula is withdrawn from the pleural cavity while the liquid sealant is being injected into the pleural cavity.

3. The method of claim 1, wherein the cannula is withdrawn from the pleural cavity after the liquid sealant has been injected into the pleural cavity.

4. The method of claim 3, comprising injecting the liquid sealant into the pleural cavity while a surgical tool is arranged within the lumen of the cannula.

5. The method of claim 4, wherein the surgical tool comprises an ablation probe.

6. The method of claim 4, wherein the surgical tool comprises a biopsy needle.

7. The method of claim 1, wherein the liquid sealant comprises one of blood or blood plasma.

8. The method of claim 1, wherein the liquid sealant comprises one of saline or water.

9. The method of claim 1, comprising inserting a surgical tool into the pleural cavity via the lumen of the cannula, wherein more liquid sealant is injected into the cannula after the surgical tool is inserted into the pleural cavity.

10. The method of claim 9, wherein the cannula comprises a valve that restricts fluid flow from the first opening of the lumen to an exterior environment, wherein the valve is actuated to an open position to receive the surgical tool and the valve is actuated to a closed position to create a seal with the ablation probe.

11. A percutaneous cannula device kit, comprising:
a reservoir containing a liquid sealant; and
a cannula device comprising:
a housing including a distal housing opening and a proximal housing opening connected by a housing lumen;

a cannula to insert through the distal housing opening, wherein the cannula includes a proximal cannula opening and a distal cannula opening connected by a cannula lumen; and
wherein the housing or cannula lumen includes a side-port opening to fluidically couple the reservoir to the housing or cannula lumen, and
wherein the side-port opening is disposed between the proximal housing opening and the distal cannula opening.

12. The percutaneous cannula device kit of claim 11, wherein the housing or cannula lumen includes a valve to prevent fluid from exiting the housing via the proximal housing opening.

13. The percutaneous cannula device kit of claim 12, wherein the side-port opening includes a second valve to prevent fluid from exiting the housing or cannula lumen via the side-port opening.

14. The percutaneous cannula device kit of claim 11, wherein the liquid sealant is at least one of: saline, plasma, blood, or water.

15. The percutaneous cannula device kit of claim 11, further comprising a surgical tool to insert through the cannula during a percutaneous lung procedure.

16. The percutaneous cannula device kit of claim 15, wherein the surgical tool comprises an ablation probe.

17. The percutaneous cannula device kit of claim 15, wherein the surgical tool comprises a biopsy needle.

18. The percutaneous cannula device kit of claim 15, wherein the housing or cannula lumen includes a valve to form a fluid tight seal around a shaft of the surgical tool.

19. The percutaneous cannula device kit of claim 18, wherein the valve is actuatable between an open position and a closed position to receive the shaft of the surgical tool.

* * * * *